United States Patent
Shioya et al.

(10) Patent No.: US 10,603,667 B2
(45) Date of Patent: Mar. 31, 2020

(54) AUTOMATIC ANALYSIS DEVICE AND CLEANING MECHANISM IN AUTOMATIC ANALYSIS DEVICE

(71) Applicant: Hitachi High-Technologies Corporation, Minato-ku, Tokyo (JP)

(72) Inventors: Kei Shioya, Tokyo (JP); Masahiko Iijima, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 16/484,185

(22) PCT Filed: Feb. 15, 2018

(86) PCT No.: PCT/JP2018/005243
§ 371 (c)(1),
(2) Date: Aug. 7, 2019

(87) PCT Pub. No.: WO2018/155300
PCT Pub. Date: Aug. 30, 2018

(65) Prior Publication Data
US 2019/0351424 A1   Nov. 21, 2019

(30) Foreign Application Priority Data

Feb. 22, 2017   (JP) ................................. 2017-030612

(51) Int. Cl.
*B01L 9/00*   (2006.01)
*B01L 3/00*   (2006.01)
(Continued)

(52) U.S. Cl.
CPC .............. *B01L 13/02* (2019.08); *B01L 3/502* (2013.01); *B08B 9/087* (2013.01); *B08B 9/093* (2013.01);
(Continued)

(58) Field of Classification Search
CPC .... B01L 13/02; B01L 3/502; B01L 2200/141; B01L 2200/16; B01L 2300/0609;
(Continued)

(56) References Cited

U.S. PATENT DOCUMENTS

| 5,948,358 A | 9/1999 | Saito |
| 2005/0058577 A1 | 3/2005 | Micklash, II et al. |

(Continued)

FOREIGN PATENT DOCUMENTS

| JP | 1-77953 U | 5/1989 |
| JP | 10-62431 A | 3/1998 |

(Continued)

OTHER PUBLICATIONS

International Search Report (PCT/ISA/210) issued in PCT Application No. PCT/JP2018/005243 dated Apr. 3, 2018 with English translation (four (4) pages).

(Continued)

*Primary Examiner* — Dennis White
(74) *Attorney, Agent, or Firm* — Crowell & Moring LLP

(57) ABSTRACT

Provided are a device and a cleaning mechanism for a reaction container in the device that are characterized by being provided with: a reaction disk for holding a reaction container; a sample dispensing mechanism for dispensing a sample to the reaction container; a reagent dispensing mechanism for dispensing a reagent to the reaction container; an optical system comprising a light source for applying light to a mixture of the sample and the reagent dispensed to the reaction container, and a detector for detecting the light applied from the light source; and a cleaning mechanism for cleaning the reaction container, wherein the cleaning mechanism is provided with a cleaning liquid supply nozzle for supplying a cleaning liquid to the reaction container after an analysis, a cleaning liquid suction (Continued)

nozzle for suctioning the supplied cleaning liquid, and a cleaning tip provided on the lower end of the cleaning liquid suction nozzle, and the side surface of the cleaning tip is formed such that the width of the cleaning tip becomes smaller downward, in the state where the cleaning tip is inserted into the reaction container, in at least a surface opposing the light source and a surface opposing the detector, and in a range that overlaps with a photometric range in which light applied to the reaction container from the light source passes through the reaction container toward the detector or in a range that is larger than the photometric range.

7 Claims, 13 Drawing Sheets

(51) Int. Cl.
*B08B 9/087* (2006.01)
*B08B 9/093* (2006.01)
*G01N 35/04* (2006.01)
(52) U.S. Cl.
CPC ........ *G01N 35/04* (2013.01); *B01L 2200/141* (2013.01); *B01L 2200/16* (2013.01); *B01L 2300/0609* (2013.01); *B01L 2300/0663* (2013.01); *B01L 2300/0803* (2013.01); *B08B 2209/08* (2013.01); *G01N 2035/0437* (2013.01); *G01N 2035/0444* (2013.01)

(58) Field of Classification Search
CPC ..... B01L 2300/0663; B01L 2300/0803; B08B 9/087; B08B 9/093; B08B 2209/08; G01N 35/04; G01N 2035/0437; G01N 2035/0444; G01N 35/02
See application file for complete search history.

(56) References Cited

U.S. PATENT DOCUMENTS

2009/0068063 A1* 3/2009 Chiba .................... G01N 35/04
422/68.1
2015/0125940 A1 5/2015 Oguro et al.

FOREIGN PATENT DOCUMENTS

| | | |
|---|---|---|
| JP | 2009-53125 A | 3/2009 |
| JP | 2015-87345 A | 5/2015 |
| JP | 2015-132520 A | 7/2015 |

OTHER PUBLICATIONS

Japanese-language Written Opinion (PCT/ISA/237) issued in PCT Application No. PCT/JP2018/005243 dated Apr. 3, 2018 (six (6) pages).
Japanese-language International Preliminary Report on Patentability (PCT/IPEA/409) issued in PCT Application No. PCT/JP2018/005243 dated Aug. 9, 2018 (four (4) pages).

* cited by examiner

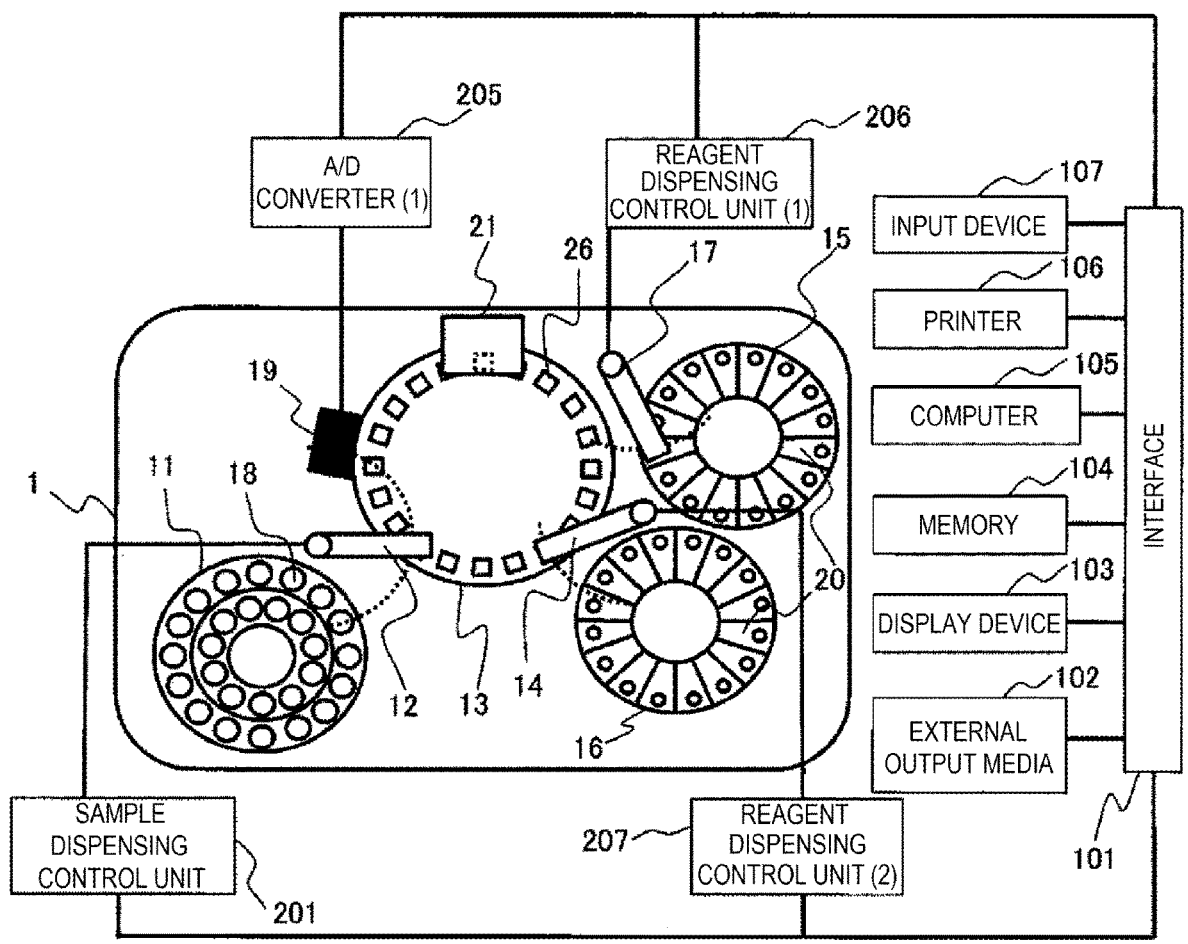
[FIG. 1]

[FIG. 2]
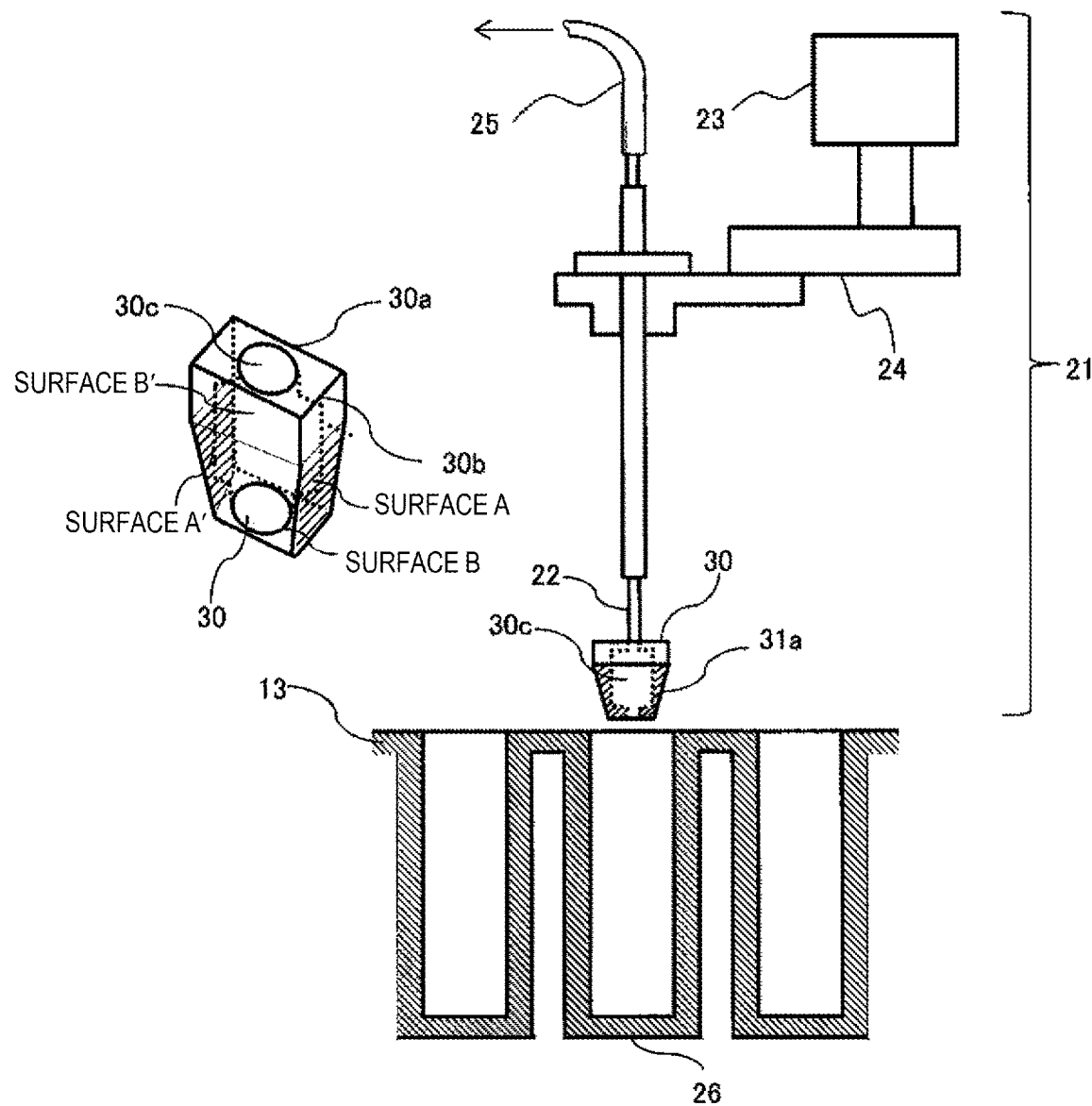

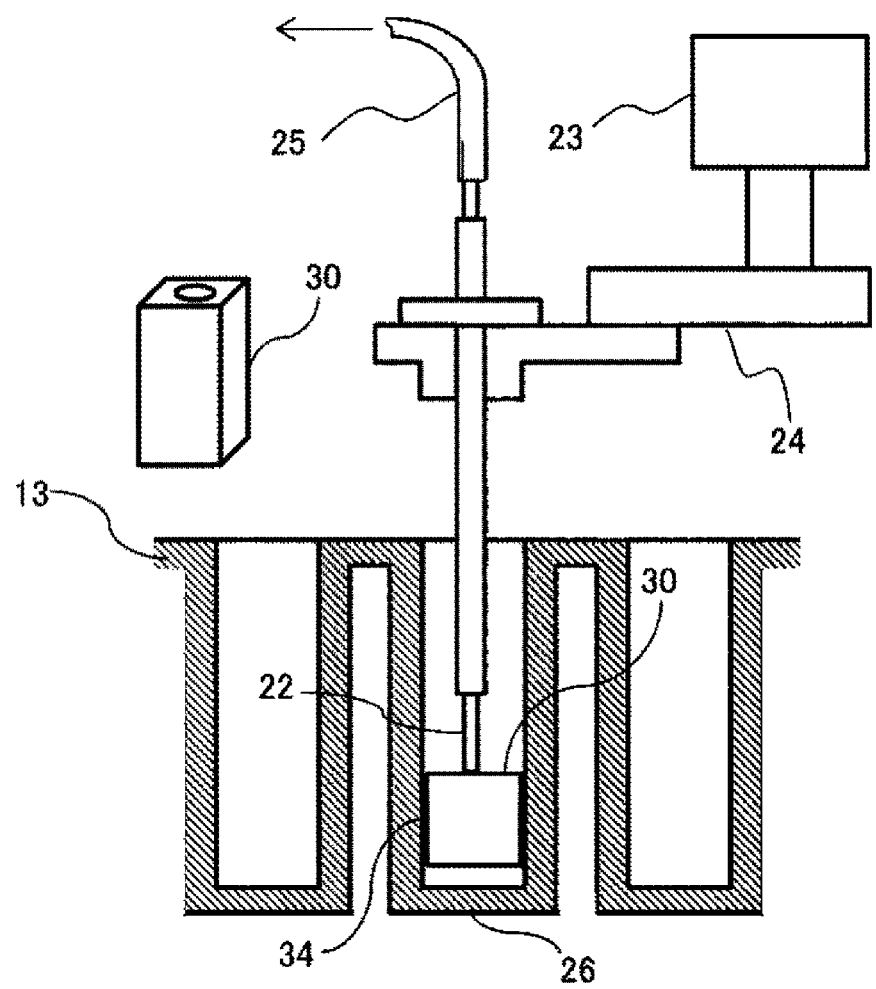
[FIG. 3]

[FIG. 4]
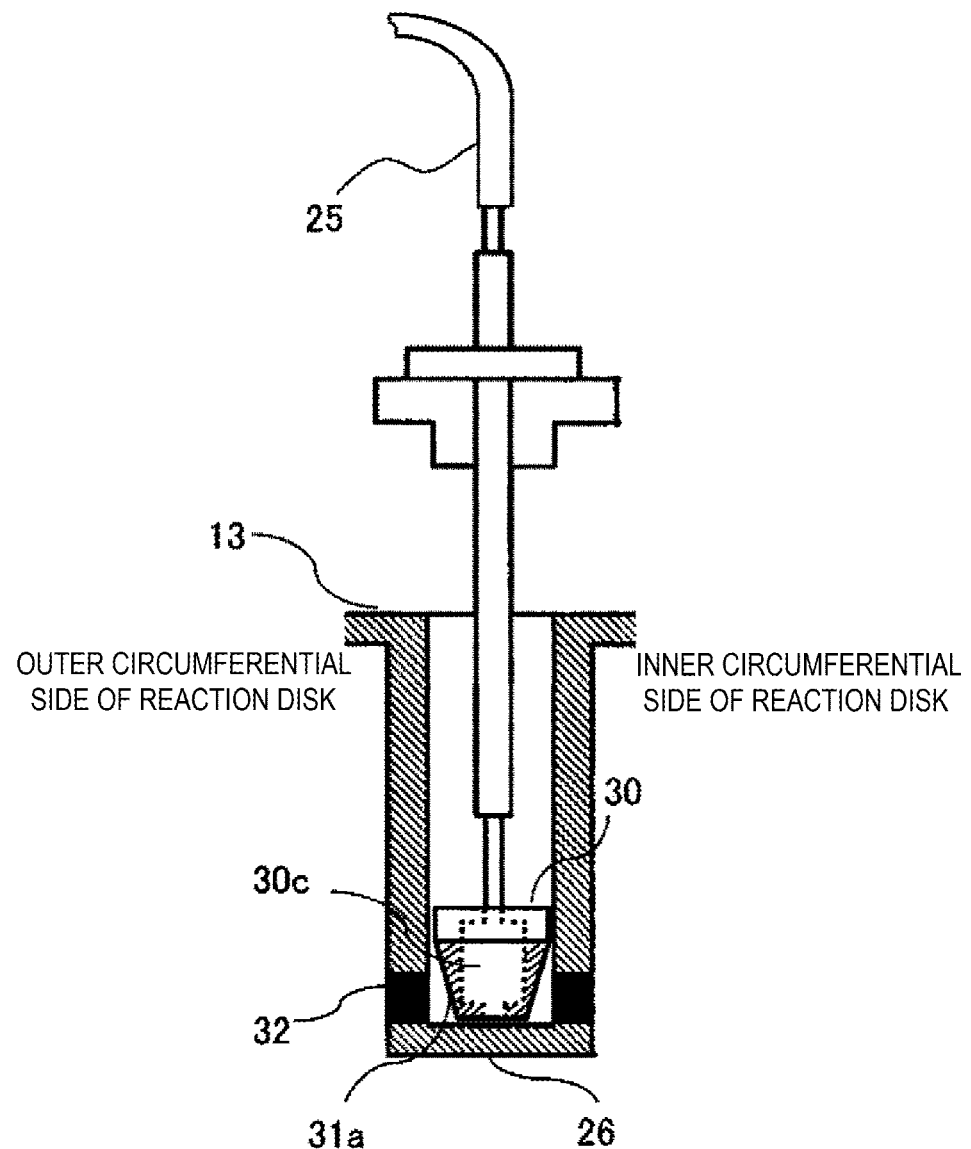

[FIG. 5]
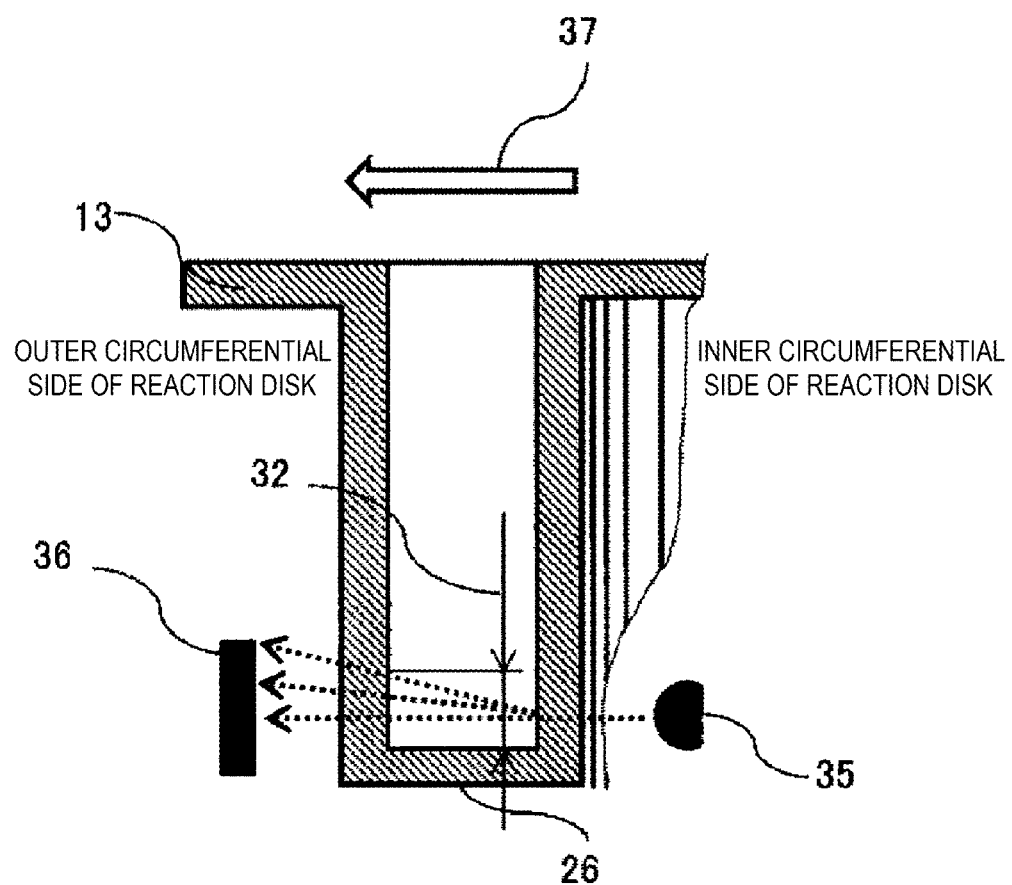

[FIG. 6]
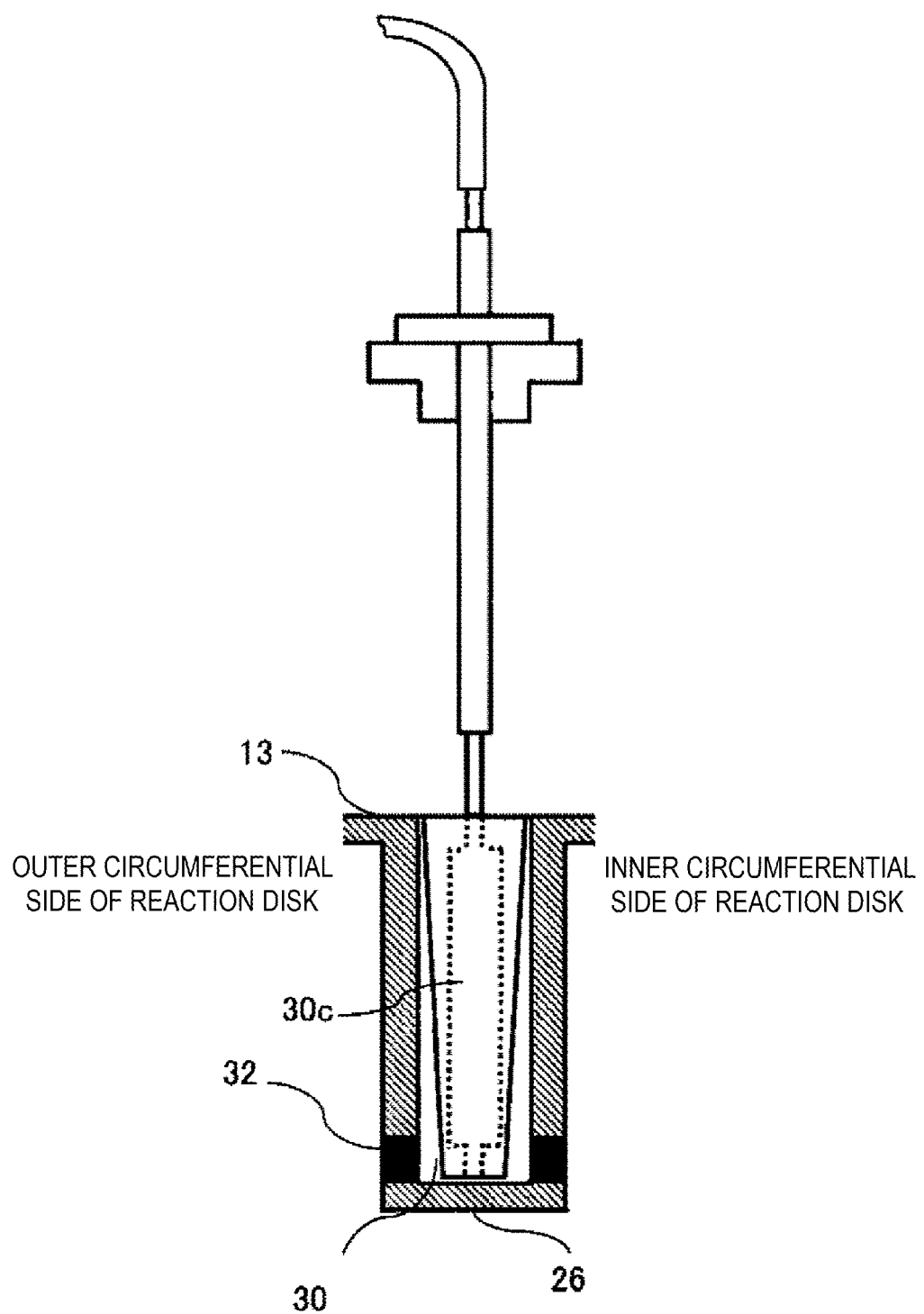

[FIG. 7]
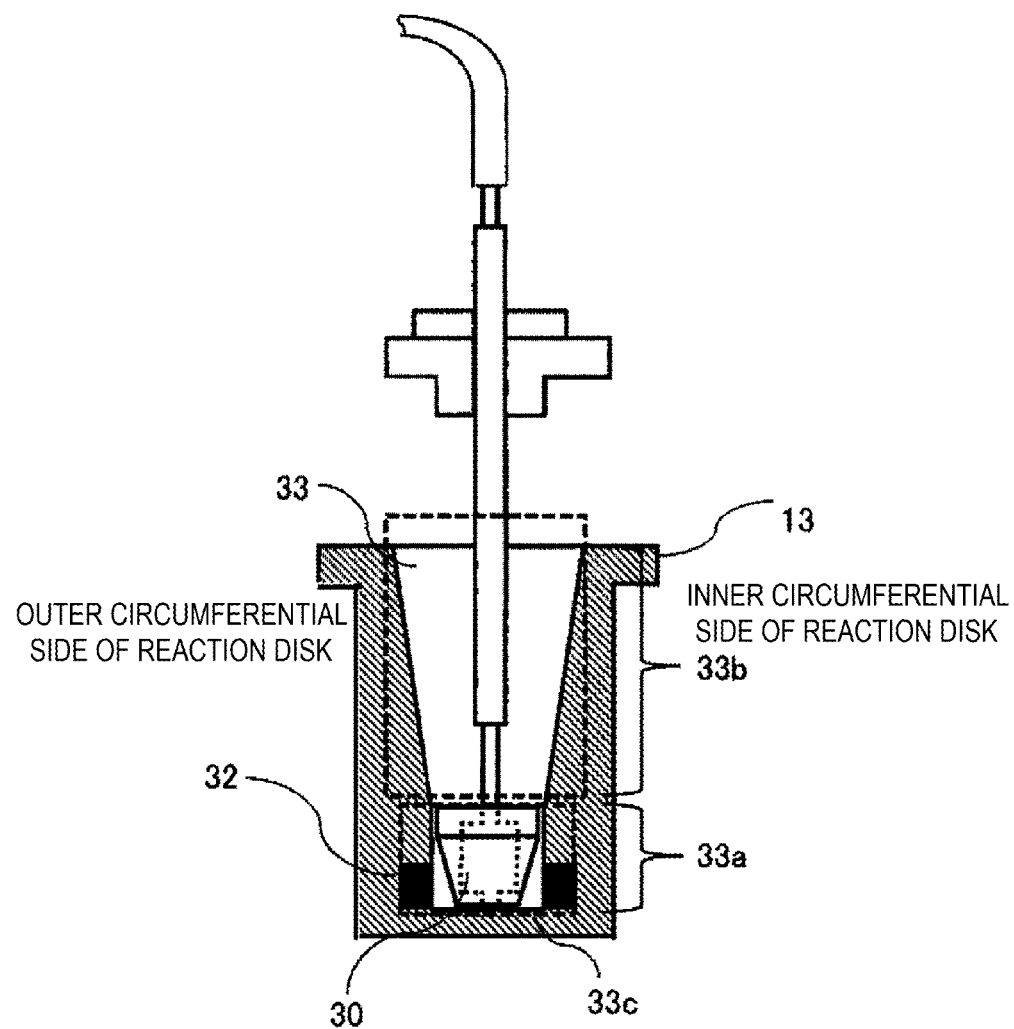

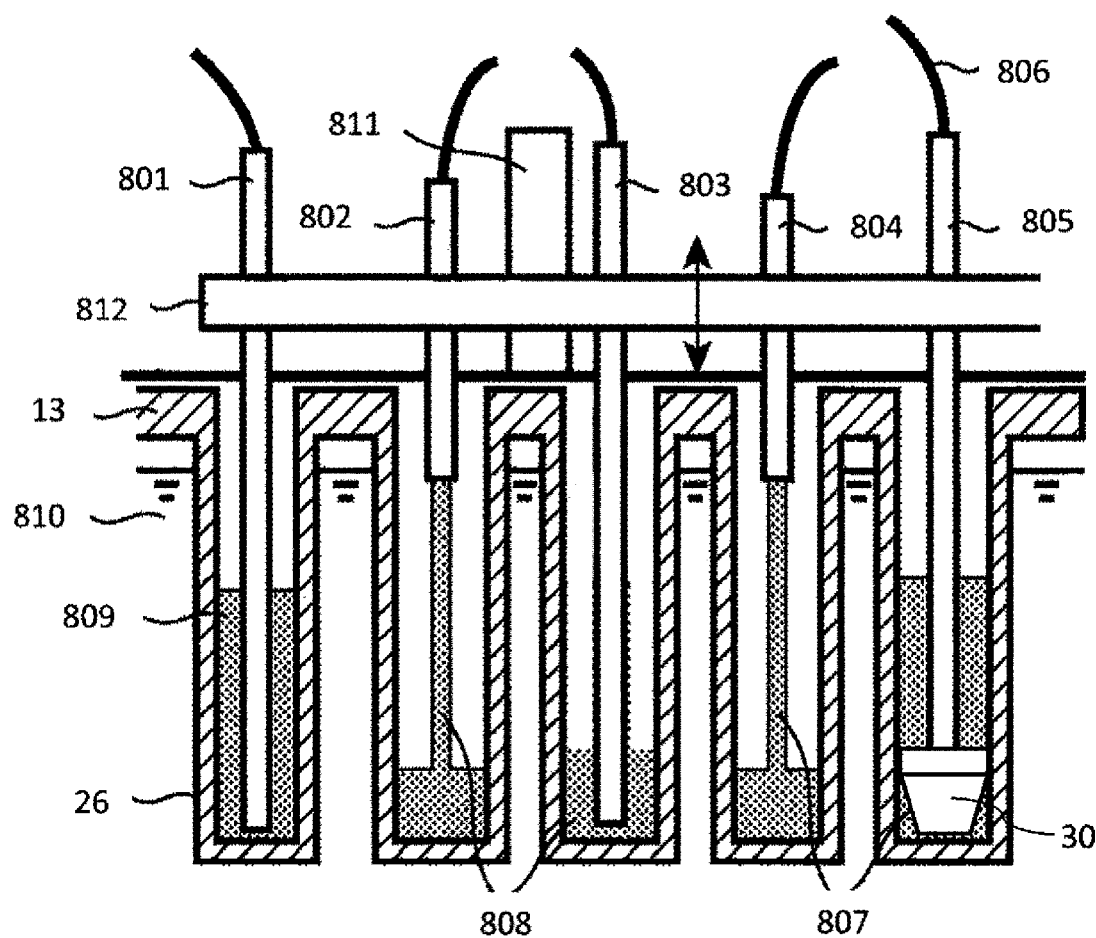
[FIG. 8]

[FIG. 9]
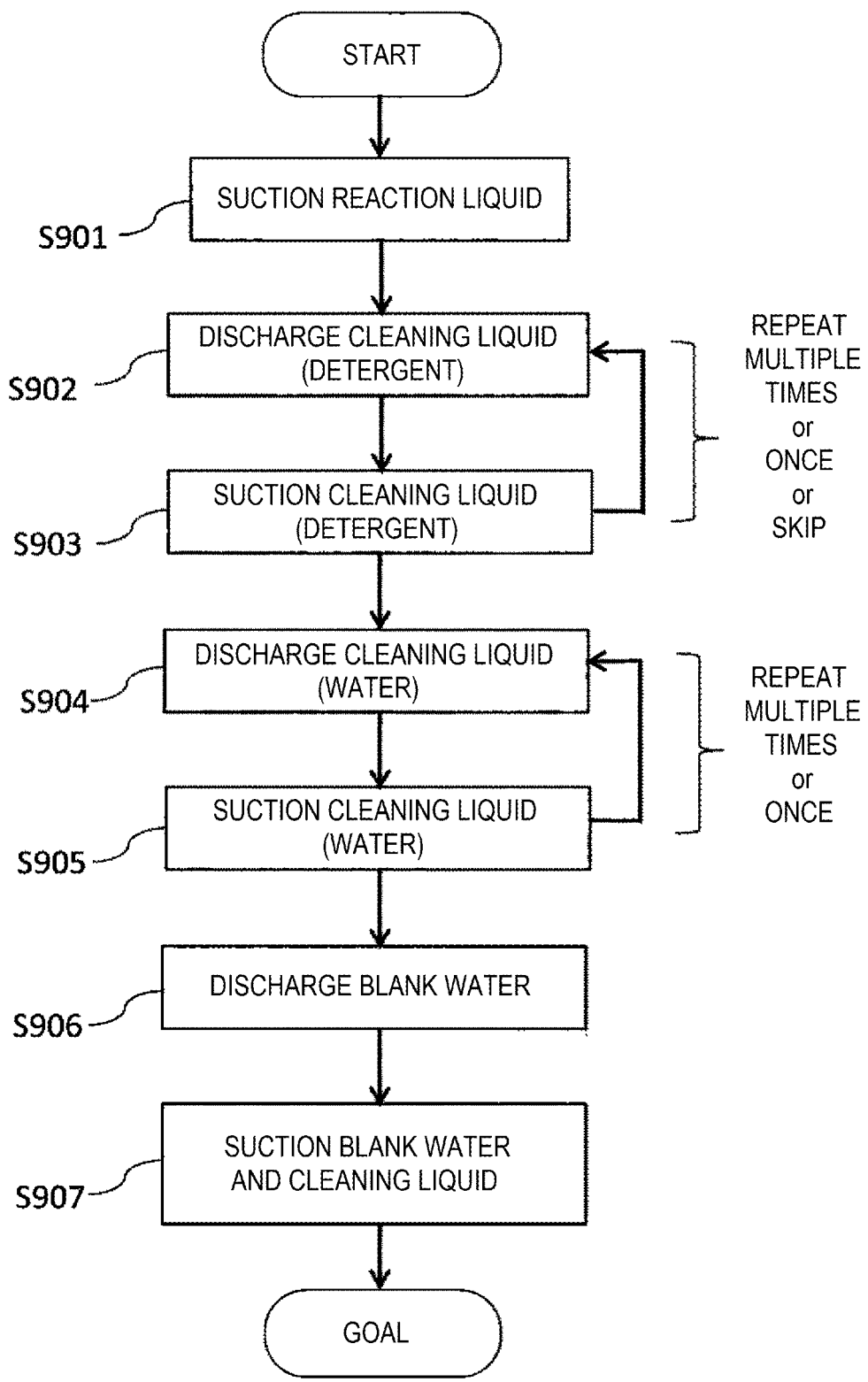

[FIG. 10]
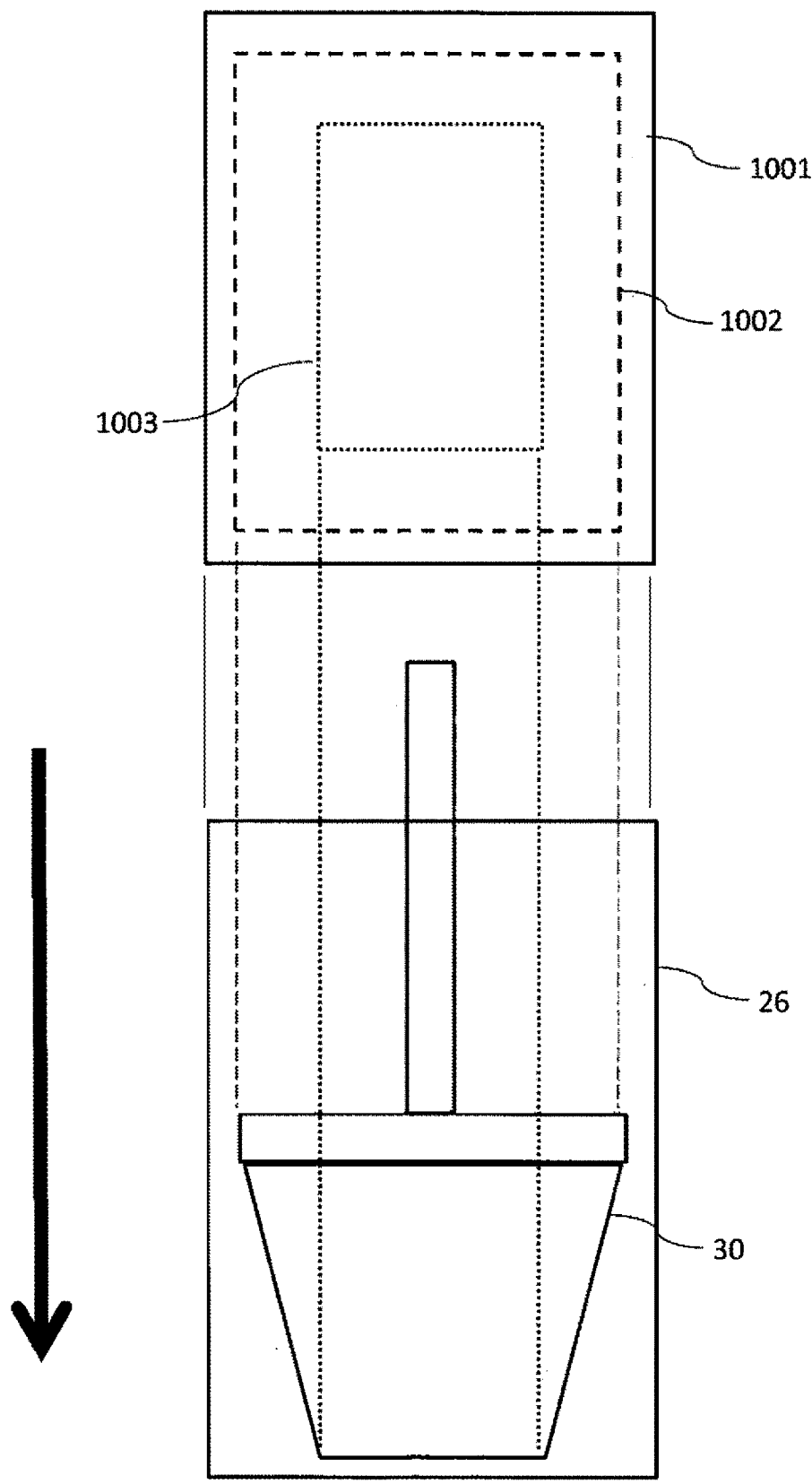

[FIG. 11]
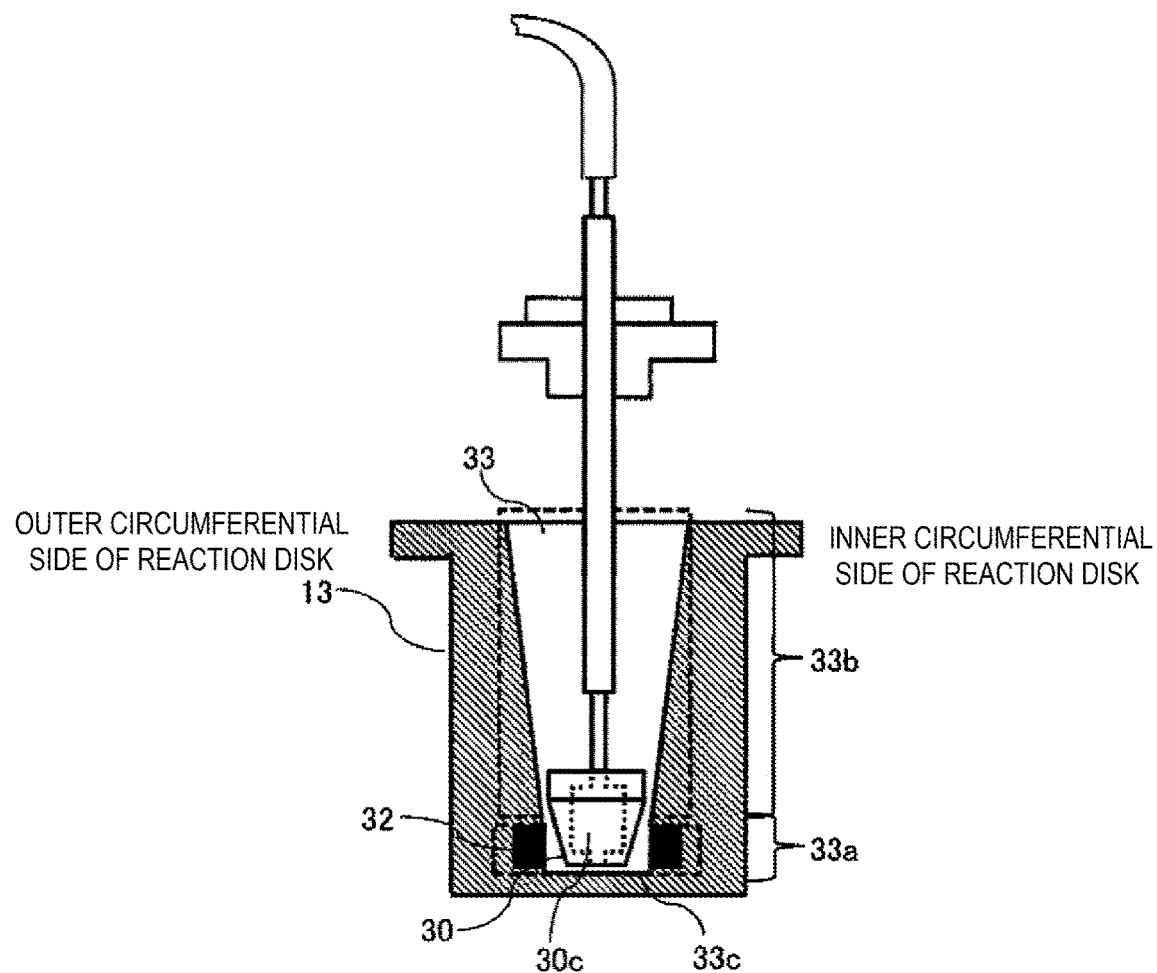

FIG. 12A   FIG. 12B   FIG. 12C
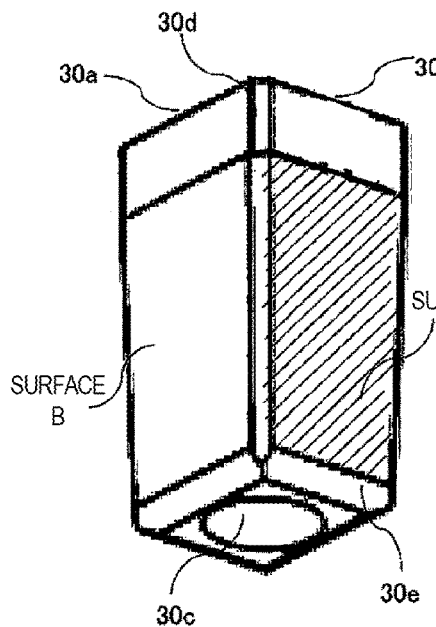 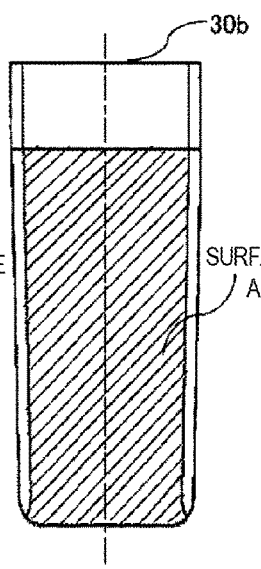 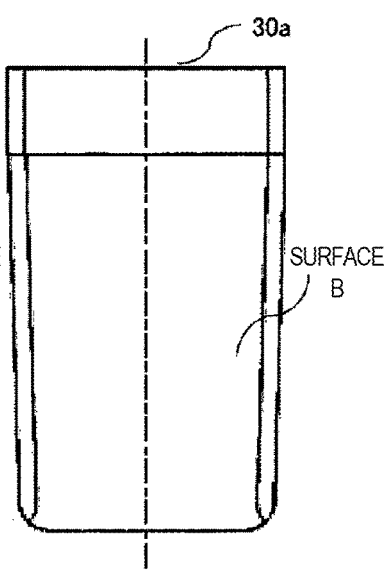
FIG. 12D   FIG. 12E
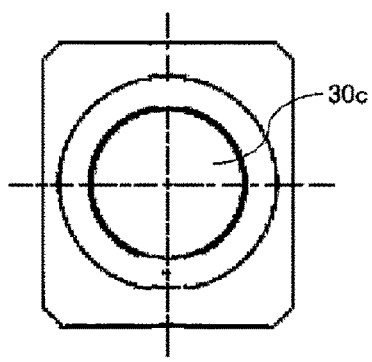 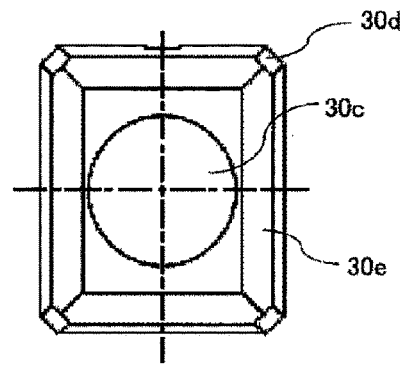

[FIG. 13]

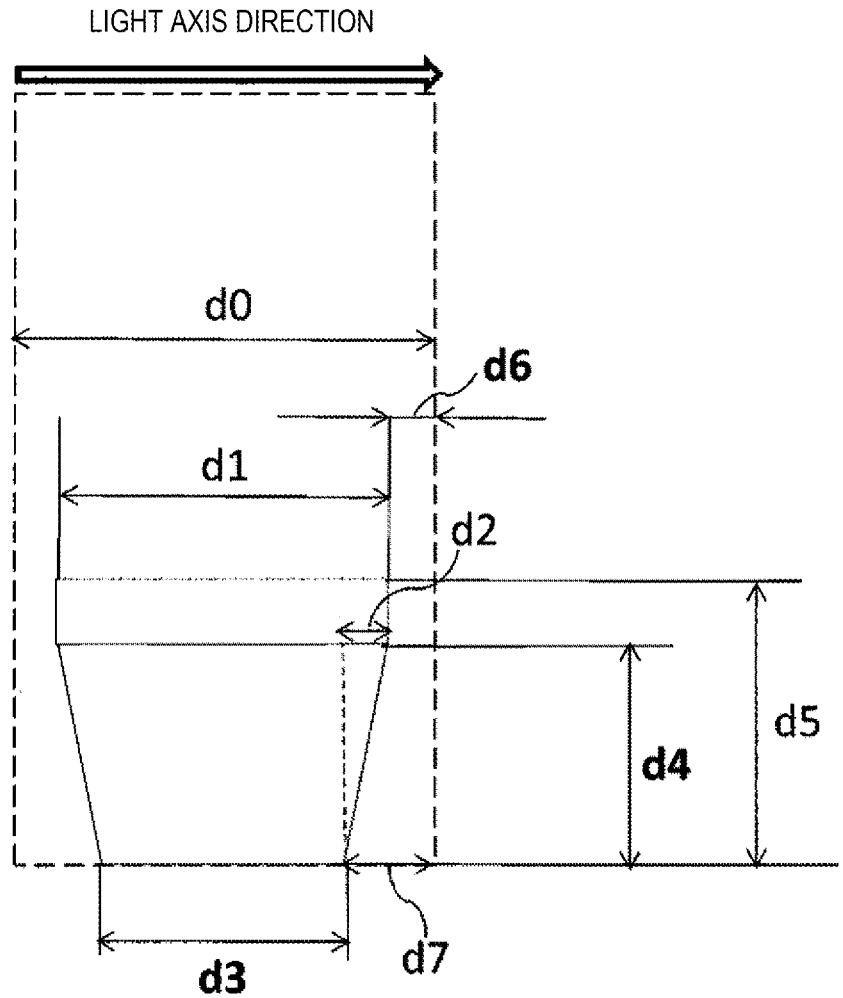

- d0 WIDTH OF REACTION CONTAINER [mm]
- d1 WIDTH OF CLEANING TIP UPPER END PART [mm]
- d2 WIDTH OF CLEANING TIP UPPER END PART - CLEANING TIP BOTTOM SURFACE (d1 - d3) [mm]
- d3 CLEANING TIP BOTTOM SURFACE [mm]
- d4 HEIGHT OF TAPER [mm]
- d5 HEIGHT OF CLEANING TIP [mm]
- d6 CLEARANCE BETWEEN REACTION CONTAINER UPPER END PART AND CLEANING TIP UPPER END PART (d0 - d1) [mm]
- d7 CLEARANCE BETWEEN REACTION CONTAINER LOWER END PART AND CLEANING TIP LOWER END PART (d0 - d3) [mm]

AUTOMATIC ANALYSIS DEVICE AND CLEANING MECHANISM IN AUTOMATIC ANALYSIS DEVICE

TECHNICAL FIELD

The present invention relates to an automatic analysis device for analyzing biological samples such as blood and urine, and particularly relates to a cleaning mechanism for cleaning a reaction container and an automatic analysis device which includes the cleaning mechanism.

BACKGROUND ART

The automatic analysis device is a device which qualitatively and quantitatively analyzes a biological sample (hereinafter, sometimes referred to as a sample) such as blood or urine. The sample is reacted with a reagent in a reaction container, and a component to be measured in the sample is analyzed. The reaction container is formed of a material such as plastic or glass, and in particular, in a device which analyzes items such as biochemical analysis, the reaction container used for measurement once is commonly cleaned and used repeatedly. In an operation of cleaning a reaction container, the reaction container is moved to a predetermined cleaning position, a cleaning liquid such as detergent or clean water is repeatedly injected and suctioned, and finally, the liquid in the reaction container is suctioned and the cleaning is finished. At this time, if remaining liquid remains in the reaction container after the cleaning, a next analysis result is affected.

As a technique for preventing the remaining liquid such as the cleaning liquid from remaining in the reaction container, in Patent Literature 1, a suck up member (hereinafter, sometimes referred to as a cleaning tip) shaped along an inner wall of the reaction container is attached to a leading end of a nozzle. The remaining liquid can be reduced by reducing a gap (hereinafter, sometimes referred to as a clearance) between the cleaning tip and the inner wall of the reaction container as much as possible. In addition, Patent Literature 2 describes a technique for reliably inserting a nozzle into a reaction container regardless of a stop accuracy of the reaction container by providing a positioning guide configured to correct and obtain a correct insertion position even when a stop position of the reaction container is deviated so as to reliably insert a cleaning tip into the reaction container.

PRIOR ART LITERATURE

Patent Literature

PTL 1: JP-A-10-062431
PTL 2: JP-A-2009-53125

SUMMARY OF INVENTION

Technical Problem

In the automatic analysis device, it is increasingly demanded to simplify a mechanism thereby reducing the size of the device, and to improve reliability of the analysis result. In a general analysis method using the automatic analysis device, light is applied from the outside of the reaction container to a mixture of a biological sample and a reagent, and the concentration of the component to be measured is calculated by detecting the transmitted and scattered light. For this reason, in a case where remaining liquid such as reaction liquid of the previous measurement or the detergent is in the reaction container which is cleaned and repeatedly used, a next measurement may be affected. In addition, there is a concern that the analysis result may be affected when the inner wall of the reaction container is scratched due to contact with the cleaning tip, and a refractive index of incident light, the transmitted light, and the scattered light is changed.

In the above-described Patent Literature 1, a clearance between the reaction container and the cleaning tip is reduced so as to reduce the remaining liquid. However, it is considered that when the clearance is reduced, the positioning becomes difficult and the cleaning tip cannot be inserted into the reaction container.

Further, although the cleaning tip can be reliably inserted into the reaction container by providing a position correction function according to the positioning guide as described in Patent Literature 2, a more complicated mechanism is required as the cleaning mechanism. Further, even if the cleaning tip can be reliably inserted into the reaction container, since the clearance between the reaction container and the cleaning tip is small, the cleaning tip may come into contact with the inner wall of the reaction container after insertion, which is not considered.

In view of the above problems, the invention is related to the implementation of a highly reliable and accurate analysis by inserting a cleaning tip with high positional accuracy and not scratching the inner wall of the reaction container without using a complicated configuration.

Solution to Problem

As an aspect for solving the above problem, an automatic analysis device for analyzing a sample based on light detected by a detector, and a cleaning mechanism for a reaction container in the automatic analysis device are provided, the automatic analysis device including: a reaction disk configured to hold a reaction container; a sample dispensing mechanism configured to dispense the sample to the reaction container; a reagent dispensing mechanism configured to dispense a reagent to the reaction container; an optical system including a light source which applies light to a mixture of the sample and the reagent dispensed to the reaction container, and the detector which detects the light applied from the light source; and a cleaning mechanism configured to clean the reaction container, wherein the cleaning mechanism includes a cleaning liquid supply nozzle which supplies a cleaning liquid to the reaction container after an analysis, a cleaning liquid suction nozzle which suctions the supplied cleaning liquid, and a cleaning tip provided on a lower end of the cleaning liquid suction nozzle, and a side surface of the cleaning tip is formed such that the width of the cleaning tip becomes smaller downward, in a state where the cleaning tip is inserted into the reaction container, in at least a surface opposing the light source and a surface opposing the detector, and in a range that overlaps with a photometric range in which light applied to the reaction container from the light source passes through the reaction container toward the detector or in a range that is larger than the photometric range.

Advantageous Effect

According to the above aspect, due to the tapered structure, the cleaning tip can be inserted with high accuracy without scratching the inner wall of the reaction container serving as the photometric region. Thus, remaining water in the reaction container is reduced without using a complicated configuration, which contributes to the implement of the highly reliable and accurate analysis.

BRIEF DESCRIPTION OF DRAWINGS

FIG. 1 is a diagram illustrating a basic configuration of an automatic analysis device according to an embodiment.

FIG. 2 is a diagram illustrating the configuration of a cleaning mechanism including a cleaning tip according to the embodiment (first embodiment).

FIG. 3 is a diagram illustrating the configuration of the cleaning mechanism including a rectangular parallelepiped cleaning tip.

FIG. 4 is a conceptual diagram illustrating a state of the cleaning mechanism including the cleaning tip during suction of a cleaning liquid according to the embodiment (first embodiment).

FIG. 5 is a diagram illustrating the configuration of a light source and a detector of a photometer according to the embodiment (first embodiment).

FIG. 6 is a diagram illustrating the configuration of a cleaning mechanism including a cleaning tip according to an embodiment (second embodiment).

FIG. 7 is a diagram illustrating the configuration of a reaction container according to an embodiment (third embodiment).

FIG. 8 is a diagram illustrating the entire configuration of the cleaning mechanism according to the embodiment.

FIG. 9 is a flow chart showing a cleaning operation according to the embodiment.

FIG. 10 is a diagram showing a relationship of cross-sectional area between the reaction container and the cleaning tip according to the embodiment.

FIG. 11 is a diagram illustrating the configuration of the reaction container according to the embodiment (third embodiment).

FIGS. 12A to 12E are diagrams illustrating details of the configuration of the cleaning tip according to the embodiment.

FIG. 13 is a diagram showing an inclination angle of a taper of the cleaning tip according to the embodiment.

DESCRIPTION OF EMBODIMENTS

Hereinafter, embodiments of the invention will be described in detail with reference to the drawings. Throughout the whole specification, components in the drawings having the same function are denoted by the same reference numeral in principle, and a description thereof may be omitted.

First Embodiment

Overall Configuration of Device

FIG. 1 is a diagram illustrating a basic configuration of an automatic analysis device according to the embodiment. Here, an example of a turntable type biochemical analysis device will be described as an aspect of the automatic analysis device.

As shown in FIG. 1, in the automatic analysis device 1, a reaction disk 13, a sample disk 11, a first reagent disk 15, a second reagent disk 16, a photometer 19, and a cleaning mechanism 21 are disposed on a housing.

The reaction disk 13 is a disk-shaped unit that can be rotated clockwise or counterclockwise, and a plurality of reaction containers 26 can be arranged on the circumference thereof.

The sample disk 11 is a disk-shaped unit that can be rotated clockwise or counterclockwise, and a plurality of sample containers 18 containing biological samples such as standard samples and test samples can be arranged on the circumference thereof.

The first reagent disk 15 and the second reagent disk 16 are disk-shaped units that can be rotated clockwise or counterclockwise, and a plurality of reagent containers 20 containing reagents containing components that react with components of each test items included in the sample can be arranged on the circumference thereof. In addition, although not shown in the drawing, the first reagent disk 15 and the second reagent disk 16 can be provided with a cooling mechanism or the like, so that the reagent arranged in the reagent container 20 can be cooled.

A sample dispensing probe 12 is disposed between the reaction disk 13 and the sample disk 11, and is arranged such that samples in the reaction containers 26 on the reaction disk 13 and the sample containers 18 on the sample disk 11 can be suctioned and dispensed by a rotation operation of the sample dispensing probe 12.

Similarly, a first reagent dispensing probe 17 is disposed between the reaction disk 13 and the first reagent disk 15, and a second reagent dispensing probe 14 is disposed between the reaction disk 13 and the second reagent disk 16. According to respective rotation operations, dispensing operations such as suction and discharge in the reaction container 26 on the reaction disk 13, and reagent containers 20 on the first reagent disk 15 and the second reagent disk 16 can be performed.

As described later with reference to FIG. 5 as an example, the photometer 19 is disposed such that a detector 36 and a light source 35 are positioned respectively on an outer peripheral side and an inner peripheral side of the reaction container 26 which is provided in the reaction disk 13, and is configured to perform photometry on transmitted light, scattered light and the like of a liquid in the reaction container 26.

The cleaning mechanism 21 is in a position which does not interfere with the sample dispensing probe 12, the first reagent dispensing probe 17, and the second reagent dispensing probe 14, and a cleaning liquid suction nozzle 22 to be described later in FIG. 2 is provided at a position where the cleaning mechanism 21 can be inserted into the reaction container 26 provided in the reaction disk 13.

Next, a control system and a signal processing system according to the automatic analysis device 1 will be briefly described. A computer 105 is connected to a sample dispensing control unit 201, a reagent dispensing control unit (1) 206, a reagent dispensing control unit (2) 207, and an A/D converter 205 via an interface 101, so as to transmit a signal which is a command to each control unit.

The sample dispensing control unit 201 controls a sample dispensing operation performed by the sample dispensing probe 12 based on a command received from the computer 105.

In addition, the reagent dispensing control unit (1) 206 and the reagent dispensing control unit (2) 207 controls a reagent dispensing operation performed by the first reagent dispensing probe 17 and the second reagent dispensing probe 14 based on a command received from the computer 105.

A photometric value of the transmitted light or scattered light of the reaction liquid in the reaction container 26 which is converted into a digital signal by the A/D converter 205 is taken into the computer 105.

A printer 106 for printing when outputting a measurement result as a report or the like, a memory 104 as a storage device or an external output medium 102, an input device 107 such as a keyboard for inputting an operation command and the like, and a display device 103 for displaying a screen are connected to the interface 101. The display device 103 is, for example, a liquid crystal display, a CRT display, or the like.

Here, a basic operation of the automatic analysis device 1 will be described.

First, an operator requests a test item for each sample by using the input device 107 such as a keyboard. In order to analyze the sample for a requested test item, the sample dispensing probe 12 dispenses a predetermined amount of sample from the sample container 18 to the reaction container 26 in accordance with an analysis parameter. The reaction container 26 to which the sample is dispensed is transferred by rotation of the reaction disk 13, and stops at a reagent receiving position. The nozzles of the first reagent dispensing probe 17 and the second reagent dispensing probe 14 dispense a predetermined amount of reagent liquid into the reaction container 26 in accordance with the analysis parameter of the corresponding test item. An order of dispensing the sample and the reagent may be different from that in the example, and the reagent may be dispensed before the sample.

Then, the sample and the reagent are stirred and mixed by a stirring mechanism (not shown). When the reaction container 26 crosses the photometric position, photometry is performed on the transmitted light or scattered light of the reaction liquid by the photometer 19. The transmitted light or scattered light subjected to photometry is converted into data of a value proportional to the light amount by the A/D converter 205, and is taken into the computer 105 via the interface 101.

By using this converted value, density data is calculated based on a calibration curve measured in advance by an analysis method specified for each test item. Component concentration data as an analysis result of each test item is output to the printer 106 or a screen of the display device 103. Before the above measurement operations are executed, the operator sets various parameters necessary for the analysis, and entries the reagent and the sample via an operation screen of the display device 103. In addition, the operator confirms the analysis result after the measurement by the operation screen on the display device 103.

Configuration of Cleaning Mechanism

Next, the entire configuration of the cleaning mechanism and the configuration of the cleaning liquid suction nozzle provided with the cleaning tip and cleaning operation according to the embodiment will be described with reference to FIG. 8, FIG. 2, FIG. 12, FIG. 9, and FIG. 13.

First, as shown in FIG. 8, the cleaning mechanism 21 mainly includes a reaction liquid suction nozzle 801 configured to suction a reaction liquid 809, a cleaning liquid discharge nozzle 802 configured to discharge a cleaning liquid 808, a cleaning liquid suction nozzle 803 configured to suction the cleaning liquid, a blank water discharge nozzle 804 configured to discharge blank water 807, a cleaning liquid suction nozzle (cleaning tip attached) 805 configured to suction the blank water 807 and the cleaning liquid used so far (also referred to as a blank water suction nozzle, and is equivalent to the cleaning liquid suction nozzle 22 described later in FIG. 2), tubes 806 connected to each of the nozzles, a nozzle jig 812 in which each nozzle is provided, and a vertical support shaft 811 configured to vertically move each nozzle. During the analysis operation, leading ends of the nozzles 801, 802, 803, 804, and 805 are positioned above the opening part of the reaction container 26, and are moved downward when the reaction disk 13 rotates to move the reaction container 26 to a predetermined cleaning position, after the suction of the reaction liquid, the discharge and suction of the cleaning liquid based on the cleaning conditions set in accordance with each analysis are performed by the respective nozzles, the blank water provided in the next analysis is ejected and suctioned. Here, the nozzles for discharging and suctioning the cleaning liquid include, for example, a nozzle for discharging and suctioning acidic or alkaline detergent, cleaning water, and the like so as to adapt various cleaning conditions. Also, in the above aspect, the cleaning liquid may be suctioned by the cleaning liquid suction nozzle 803 only by a certain amount (predetermined amount) before the cleaning liquid suction nozzle 805 (cleaning tip attached) perform suction, and only the remaining cleaning liquid is suctioned by the cleaning liquid suction nozzle 805 (cleaning tip attached). In this way, the amount of the liquid to be suctioned by the cleaning liquid suction nozzle 805 (cleaning tip attached) is reduced, the suction efficiency is improved, and the remaining liquid after cleaning the inside of the reaction container 26 can be further reduced, so that the reliability of the analysis result can be further improved.

Next, the configuration of the cleaning liquid suction nozzle provided with the cleaning tip according to the embodiment will be described in more detail. As shown in FIG. 2, the mechanism configured to suction the cleaning liquid in the cleaning mechanism 21 is mainly configured by a cleaning liquid suction nozzle 22 configured to suction the cleaning liquid, a cleaning tip 30 connected to the leading end (lower end) of the cleaning liquid suction nozzle 22, a suction tube 25 connected to an end (upper end) of the cleaning liquid suction nozzle 22 on the opposite side of the cleaning tip 30, an arm 24 capable of moving up and down so as to insert the cleaning liquid suction nozzle 22 into the reaction container 26, and a motor 23 for driving the arm 24.

Here, the cleaning tip 30 is provided so that the maximum width 30*a* and thickness 30*b* can be inserted into the reaction container 26, and a taper 31 *a*, which will be described later, is provided in surface A, surface A' (shaded part), and surface B, surface B' in the figure. Here, a configuration as described above in which the taper is provided on the surface A, the surface A', the surface B, and the surface B' is described so that the positioning can be made easier, and the taper may be provided only on the surface A and the surface A' through which light for photometry passes, and not be provided on the surface B and the surface B'. In this case, it is advantageous that scratch to the inner wall of the reaction container 26 is prevented by the taper with respect to the surface A and the surface A' that have more effect the analysis result, and further, the surface B and the surface B' that have relatively small effect can be configured to have reduced clearance so that the remaining liquid can be reliably suctioned.

In addition, the cleaning tip 30 is provided with an inner hole 30*c* therein, which is a liquid flow path when the cleaning liquid is suctioned by the cleaning liquid suction nozzle 22. It is desirable that the cleaning tip 30 is made of, for example, a resin softer than the reaction container 26, and uses a material having chemical resistance.

FIG. 12 is a diagram illustrating details of the configuration of the cleaning tip according to the embodiment. For the above-described cleaning tip 30, FIG. 12(*a*) is a perspective view, FIG. 12(*b*) is a front view (A surface), FIG. 12(*c*) is a side view (B surface), FIG. 12(*d*) is a top view, and FIG. 12(*e*) is a bottom view. Here, as shown in (a), chamfered parts 30*d* and 30*e* by cutting off of the edges may be provided in corner parts of four places in the insertion direction of the cleaning tip 30 and corner parts of four places on the bottom surface. With this configuration, scratch to the inner walls and the bottom surfaces of the reaction container 26 can be further reduced, and the effect of protection can be further enhanced. The chamfered parts may be provided in all four places, and it is also possible to provide in at least one place.

FIG. 9 is a flow chart showing the cleaning operation according to the embodiment. After completion of the measurement described above, the reaction container 26 used for the measurement is moved to the cleaning position of the cleaning mechanism 21 by the rotation of the reaction disk 13, and the reaction liquid is suctioned (step S901); then, the cleaning liquid such as alkaline detergent, acid detergent, or cleaning water is discharged and suctioned in accordance with the cleaning condition (steps S902 to S905). Thus, the liquid in the reaction container 26 is replaced with the cleaning liquid from the reaction liquid. Here, steps S902 and S903 may be repeated a plurality of times or once in accordance with the cleaning condition, and may also be skipped in a case where the cleaning may be performed only by cleaning water. In addition, the steps S904 and S905 can be repeated a plurality of times or once in accordance with the cleaning condition.

After replacement with the cleaning liquid, the blank water is dispensed into the reaction container 26, and since the contamination of the reaction container 26 used for the measurement is measured by the photometer 19, it is desirable to raise an alarm for requesting replacement of the reaction container 26 when a certain threshold value is exceeded. When it is confirmed that the contamination of the reaction container 26 is lower than the threshold value, finally, the cleaning liquid suction nozzle 22 is lowered by the motor 23, inserted into the reaction container 26, and suction the liquid in the reaction container 26 via the cleaning liquid suction tube 25, so that the reaction container 26 can be used for the next measurement.

Here, damage such as the scratch to the inner wall of the reaction container 26 due to contact with the cleaning mechanism 21 including the cleaning tip 30 will be described with reference to FIG. 3. FIG. 3 is a diagram showing a configuration of a cleaning mechanism including a rectangular parallelepiped cleaning tip.

As described above, it is known that the smaller the clearance between the outer wall of the cleaning tip 30 and the inner wall of the reaction container 26, the less the remaining liquid at the time of suction of the cleaning liquid. Therefore, it is considered that the remaining liquid will be less by configuring the cleaning tip 30 to have a shape along the inside of the reaction container 26, that is, configuring the cleaning tip 30 to have a rectangular parallelepiped shape as shown in FIG. 3.

However, as shown in the figure, if the cleaning tip 30 has a rectangular parallelepiped shape, when being inserted into the reaction container 26, the cleaning tip 30 may come into contact with a part 34 of the inner wall of the reaction container 26 and cause scratching in a case where the insertion is deviated from the center of the reaction container 26 or an integration and the like due to a dimensional tolerance of a configure component. When the reaction container 26 is scratched, the light incident on the reaction container 26 and the light transmitted through or scattered through the reaction container 26 cannot be correctly measured due to a change in the refractive index caused by the scratch. Therefore, as shown in FIG. 2, in the embodiment, the side surface of the cleaning tip 30 is formed such that a width thereof becomes smaller downward, in the state where the cleaning tip 30 is inserted into the reaction container 26, in at least a surface opposing the light source and a surface opposing the detector, and in a range that overlaps with a photometric region 32 (hereinafter, also referred to as photometric range) which is a range in the height direction of the reaction container 26 when light applied to the reaction container 26 from the light source 35 passes through the reaction container 26 toward the detector 36 or in a range that is larger than the photometric range. In the embodiment, a configuration in which the taper 31*a* is provided on the side will be described as an example thereof.

Here, FIG. 4 is a conceptual diagram showing a state of the cleaning mechanism provided with the cleaning tip at the time of suctioning cleaning liquid according to the embodiment, and illustrates a relationship between the taper 31*a* in FIG. 2 and the photometric region 32 of the reaction container 26. In this figure, referring to FIG. 2, it is viewed from an angle rotated at which the right side is the inner circumferential side and the left side is the outer circumferential side of the reaction disk 13.

As shown in this figure, the taper 31*a* is provided with the width being smaller toward the leading end (lower end) of the cleaning tip 30 in a range which overlaps with or is larger than the photometric region 32 of the reaction container 26 (that is, the cross-sectional areas in planes perpendicular to the insertion direction of the cleaning tip 30 to the reaction vessel 26 become smaller downward referring to the cross-sectional area of the opening part of the reaction vessel 26 in a plane perpendicular to the insertion direction of the cleaning tip 30), so that the cleaning liquid can be suctioned without damaging the photometric region 32 of the reaction container 26.

Here, FIG. 10 is a diagram illustrating a relationship between a cross-sectional area of the reaction container and the cleaning tip according to the embodiment. As shown in this figure, the cross-sectional area of the cleaning tip 30 in a plane perpendicular to the insertion direction of the cleaning tip 30 indicated by an arrow in the figure is configured to be smaller from the upper end portion 1002 toward the lower end portion 1003 with respect to the cross-sectional area of the opening 1001 of the reaction container 26.

As described above, the photometric region 32 indicates a range in a height direction, and in this embodiment, the direction of the light applied from the light source 35 described later in FIG. 5 and the transmitted and scattered light is in a direction from front to bottom in FIG. 10. That is, the light is applied in a radial direction 37 from the inner circumferential side to the outer circumferential side of the reaction disk 13, and subjected to photometry by the detector 36 shown in FIG. 5 provided on the outer circumferential side.

FIG. 5 is a diagram illustrating a configuration of the light source and the detector of the photometer according to the embodiment. In this example, light is incident on the reaction container from the light source, and the transmitted light is detected by the detector. In addition, in this example, a configuration is described in which the light source 35 is disposed on the inner circumferential side and the detector 36 is disposed on the outer circumferential side of the reaction disk 13, and it can also be configured such that the positions of the light source 35 and the detector 36 are exchanged, that is, the light source 35 is disposed on the outer circumferential side and the detector 36 is disposed on the inner circumferential side of the reaction disk 13. As shown in this figure, since the taper 31a is provided in the cleaning tip 30 in a range that overlaps with the photometric range 32 of the reaction container 26 in which light applied from the light source 35 and towards the detector 36, or in a range larger than the photometric range 32, the cleaning tip 30 does not contact with the inner wall of the reaction container 26 in the range, so that the effect on the measurement result due to such contact can be prevented.

Here, by designing the volume of the space between the inner wall of the reaction container 26 and the outer wall of the cleaning tip 30 (hereinafter, sometimes referred to as clearance) equal to or less than the volume of the inner hole 30c of the cleaning tip 30, it is possible to maintain the ability of the cleaning liquid suction nozzle 22 to suction the cleaning liquid, and to prevent an increase of the remaining liquid due to the taper 31a.

The volume of the cleaning tip 30 itself is configured such that the cleaning liquid does not overflow from the reaction container 26 even if the cleaning tip 30 is inserted in the reaction container 26 containing the cleaning liquid. As an example, since the maximum amount of the liquid entering the reaction container 26 occupies 80% of the capacity of the reaction container 26, the volume of the cleaning tip 30 is 20% or less with respect to the capacity of the reaction container 26. According to the configuration, even in case of the cleaning liquid cannot be suctioned due to clogging of the suction tube or the like, the possibility that the cleaning liquid overflows can be reduced.

In addition, it is considered that when the cleaning tip 30 has a rectangular parallelepiped shape, the cleaning tip 30 may not be inserted due to a stop accuracy of the reaction disk 13, the dimensional tolerance of the configure component, the error of the position adjustment, and the like at the time of inserting, and the device may be caught and stopped at an entrance of the reaction container 26 at the time of lowering. On the other hand, in the cleaning tip 30 according to the embodiment, the leading end of the cleaning tip 30 has a structure smaller than the maximum width 30a and thickness 30b of the cleaning tip 30 by providing with the taper 31a, so that the clearance with the entrance of the reaction container 26 can be secured even when the cleaning tip 30 is deviated from the center of the reaction container 26, and the cleaning tip 30 can be easily inserted.

According to the configuration described above, the reliability of the analysis performance of the device can be improved without lowering a cleaning efficiency according to the taper 31a provided in the cleaning tip 30. In addition, it is possible to facilitate positioning without complicating the configuration of the device, and it is possible to realize the effect with reduced space and cost.

In addition, FIG. 13 is a diagram illustrating an inclination angle of the taper 31a of the cleaning tip 30 according to the embodiment. As shown in this figure, the larger the clearances (d6, d7) formed between the reaction container 26 and the cleaning tip 30 are, the easier it is to insert the cleaning tip 30 into the reaction container 26, which makes it difficult to scratch the photometric region, while the possibility of increase in the remaining liquid is raised. Therefore, as an example, by setting the conditions of d0 to d7 so that the inclination angle θ of the taper 31a is within a range of 1 to 5 degrees, the accuracy of positioning the cleaning tip 31 can be improved and the cleaning efficiency can be maintained.

In the first embodiment described above and second and third embodiments to be described later, a configuration in which the width of a predetermined surface of the cleaning tip becomes narrower downward continuously is described as an example of the taper 31a. However, other than this configuration, a shape in which the width becomes narrower in a stepwise manner other than continuously, for example, may also be applied to the taper 31a. Further, as an example of the cleaning tip 30, the configuration which has four side surfaces including the surface A, the surface A', the surface B, and the surface B' has been described, but other than this configuration, for example, it is also possible to apply a shape of an inverted truncated cone having one continuous side surface, and is rotated approximately 180 degrees with respect to the shape of the truncated cone so that the upper surface with a small cross-sectional area becomes the bottom surface. When the shape of inverted truncated cone is applied as the cleaning tip 30, the light to be measured by the photometer 19 is more desirably to be the scattered light than the transmitted light, and in order to fit with the shape of the cleaning tip 30, the shape of the reaction container 26 may also be configured as an inverted truncated cone.

In addition, other than the taper 31a, for example, the cleaning tip 30 having one continuous side surface may also adopt a configuration in which a curve is drawn such that the width thereof becomes smaller downward.

Second Embodiment

Next, another configuration of the cleaning mechanism 21 of the automatic analysis device 1 according to the embodiment will be illustrated. In the first embodiment described above, an example in which the height of the cleaning tip 30 is lower than the height of the reaction container 26 (height from the opening part (upper end) to the bottom surface (lower end)) is described. Here, a configuration is described with reference to FIG. 6 in which the height of the cleaning tip 30 is approximately the same as the height from the opening part to the bottom surface of the reaction container 26, and the taper 31a is provided from the upper end to the lower end of the cleaning tip 30. FIG. 6 is a diagram illustrating the configuration of the cleaning mechanism including a cleaning tip according to the embodiment (second embodiment). In this figure, similar as that in FIG. 4, with respect to FIG. 2, it is viewed from an angle rotated at which the right side is the inner circumferential side and the left side is the outer circumferential side of the reaction disk 13.

In the example shown in the drawing, as described above, the height of the cleaning tip 30 is approximately the same as the height from the opening part to the bottom surface of the reaction container 26, and the taper 31a is provided from the upper end to the lower end of the cleaning tip 30. Thus, the taper 31a provided in the range is approximately the same as the height from the opening part to the bottom surface of the reaction container 26. Here, the cross-sectional areas of the taper 31 in the planes perpendicular to the insertion direction of the cleaning tip 30 to the reaction container 26 are formed to become smaller downward with respect to the cross-sectional area from the opening part to the bottom surface of the reaction container 26.

Since the possibility that the cleaning tip 30 contacts with the inner wall of the reaction container 26 can be reduced according to the shape, not only the photometric region 32 but also the entire inner wall of the reaction container 26 can be protected. Thus, in addition to facilitating the positioning of the cleaning tip 30 as that in the first embodiment described above, it can be expected that the life of the reaction container 26, which is a consumable product, is extended, and the cost is reduced. In substantially the same degree, a configuration of a range in which the above-described effects are substantially obtained is also included.

Third Embodiment

Next, another configuration of the reaction container 26 of the automatic analysis device 1 according to the embodiment will be described. In the embodiment described above, a configuration in which the rectangular parallelepiped reaction container 26 with all the surfaces being rectangular shapes is described. Here, a case of using a reaction container (hereinafter, referred to as a taper type reaction container 33) is described with reference to FIG. 7, in which in a state where the lower end of the cleaning tip 30 is provided to be in contact with the bottom surface as a part of the reaction container, in a rectangular parallelepiped region 33a (first region) from the upper end of the cleaning tip 30 to the bottom surface of the reaction container, the cross-sectional areas in the planes perpendicular to the insertion direction of the cleaning tip 30 to the reaction container are equal, and in a taper region 33b (second region) from the upper end of the cleaning tip 30 to the opening part of the reaction vessel, the cross-sectional area of the surface increases from the upper end of the cleaning chip 30 toward the opening part of the reaction container. As shown in the figure, the taper of the taper type reaction container 33 is provided so that the cross-sectional area decreases downward, that is, toward the photometric region 32. In the figure and FIG. 11 to be described later, similarly to FIG. 4 and FIG. 6, with respect to FIG. 2, it is viewed from an angle rotated at which the right side is the inner circumferential side and the left side is the outer circumferential side of the reaction disk 13.

In addition to the example shown in the figure, the rectangular parallelepiped region 33a (first region) may be provided to have equal cross-sectional areas in planes perpendicular to the insertion direction of the cleaning tip 30 to overlap at least the photometric region 32, for example, from the upper end of the photometric region 32 shown in FIG. 11 to the bottom surface 33c of the taper type reaction container 33, and the tapered region 33b (second region) may be provided to have cross-sectional areas in planes perpendicular to the insertion direction of the cleaning tip 30 that become larger in the region positioned above the photometric region 32, that is, from the upper end of the photometric region 32 toward the opening part of the taper type reaction container 33.

Referring back to FIG. 7, the upper end of the rectangular parallelepiped region 33a of the taper type reaction container 33 is located at the same level as the upper end of the cleaning tip 30. The taper 31a of the cleaning tip 30 is provided in the rectangular parallelepiped region 33a. In the tapered region 33b provided above the rectangular parallelepiped region 33a, the size of the inlet of the taper type reaction container 33 can be designed to be larger due to the tapered structure formed such that the width becomes larger toward the opening part on the upper side (that is, the cross-sectional areas in the planes perpendicular to the insertion direction of the cleaning tip 30 become larger), and thus the positioning of the cleaning tip 30 attached to the cleaning mechanism 21 can be further facilitated.

The invention is not limited to the embodiments described above, and includes various modifications. For example, the embodiments described above have been described in detail for easy understanding of the invention, but the invention is not necessarily limited to those including all the configurations described above. Further, a part of the configuration of one embodiment can be replaced with the configuration of another embodiment, and it is also possible to add the configuration of another embodiment to the configuration of one embodiment. Part of the configuration of each embodiment may be added, deleted, or replaced with another configuration.

REFERENCE SIGN LIST 1 automatic analysis device
11 sample disk
12 sample dispensing probe
13 reaction disk
14 second reagent dispensing probe
15 first reagent disk
16 second reagent disk
17 first reagent dispensing probe
18 sample container
19 photometer
20 reagent container
21 cleaning mechanism
22 cleaning liquid suction nozzle
23 motor
24 arm
25 suction tube
26 reaction container
30 cleaning tip
30a maximum width of cleaning tip
30b maximum thickness of cleaning tip
30c inner hole of cleaning tip
30d, 30e chamfered part of cleaning tip
31a taper provided in cleaning tip
32 photometric region of reaction container (photometric range)
33 taper type reaction container
33a rectangular parallelepiped region (first region)
33b tapered region (second region)
33c bottom surface
34 contact part of inner wall of reaction container with cleaning tip
35 light source
36 detector
37 radial direction (direction from inner circumference to outer circumference) of reaction disk
101 interface
102 external output media
103 display device
104 memory
105 computer
106 printer
107 input device
201 sample dispensing control unit
205 A/D converter
206 reagent dispensing control unit (1)
207 reagent dispensing control unit (2)
801 reaction liquid suction nozzle
802 cleaning liquid discharge nozzle
803 cleaning liquid suction nozzle
804 blank water discharge nozzle
805 (cleaning tip attached) cleaning liquid suction nozzle (blank water suction nozzle)

806 tube
807 blank water
808 cleaning liquid
809 reaction liquid
810 thermostat water
811 vertical support shaft
812 nozzle jig
1001 opening part
1002 cleaning chip upper end part
1003 cleaning chip lower end part

The invention claimed is:

1. An automatic analysis device comprising:
a reaction disk configured to hold a reaction container;
a sample dispensing mechanism configured to dispense a sample to the reaction container;
a reagent dispensing mechanism configured to dispense a reagent to the reaction container;
an optical system including a light source which applies light to a mixture of the sample and the reagent dispensed to the reaction container, and a detector which detects the light applied from the light source; and
a cleaning mechanism configured to clean the reaction container,
wherein the cleaning mechanism includes a cleaning liquid supply nozzle which supplies a cleaning liquid to the reaction container after an analysis, a cleaning liquid suction nozzle which suctions the supplied cleaning liquid, and a cleaning tip provided on a lower end of the cleaning liquid suction nozzle,
a side surface of the cleaning tip is configured by, in a state where the cleaning tip is inserted into the reaction container, and in at least a surface opposing the light source and a surface opposing the detector,
a first region which includes a photometric range in which light applied to the reaction container from the light source passes through the reaction container toward the detector, and is formed such that the width becomes smaller downward, and
a second region which does not include the photometric range, positioned above the first region and have the same width as an upper end part of the first region, and
volume of a clearance between an inner wall of the reaction container and the cleaning tip is less than or equal to a volume of an inner hole of the cleaning tip.

2. The automatic analysis device according to claim 1, wherein
the first region on the side surface of the cleaning tip has a taper formed such that the width becomes smaller downward.

3. The automatic analysis device according to claim 2, wherein
the taper is formed such that an inclination angle is 1 to 5 degrees.

4. The automatic analysis device according to claim 1, wherein
the side surface includes four surfaces.

5. The automatic analysis device according to claim 4, wherein
the first region is formed only in two surfaces among the four surfaces, which are the surface opposing the light source and the surface opposing the detector.

6. The automatic analysis device according to claim 4, wherein
the side surface has at least one chamfered part which is chamfered at a corner part formed on two adjacent surfaces among the four surfaces.

7. The automatic analysis device according to claim 1, further comprising:
a control unit configured to control the cleaning mechanism, wherein
the cleaning mechanism includes the cleaning liquid supply nozzle which supplies the cleaning liquid to the reaction container after the analysis, and the cleaning liquid suction nozzle and a second cleaning liquid suction nozzle which suction the supplied cleaning liquid, and
the control unit is configured to control the cleaning mechanism such that the cleaning liquid is supplied to the reaction container after the analysis by the cleaning liquid supply nozzle, a predetermined amount of the supplied cleaning liquid is suctioned by the second cleaning liquid suction nozzle, and after the suction, the cleaning liquid remaining in the reaction container is suctioned by the cleaning tip provided in the cleaning liquid suction nozzle.

* * * * *